US006945940B1

(12) United States Patent
Chiang

(10) Patent No.: US 6,945,940 B1
(45) Date of Patent: Sep. 20, 2005

(54) CONTACT TYPE PULSE MEASUREMENT DEVICE

(75) Inventor: Cheng-Tang Chiang, Taichung (TW)

(73) Assignee: Boson Technology Co., LTD, Taichung (TW)

( * ) Notice: Subject to any disclaimer, the term of this patent is extended or adjusted under 35 U.S.C. 154(b) by 0 days.

(21) Appl. No.: 10/799,729

(22) Filed: Mar. 15, 2004

(51) Int. Cl.$^7$ ............................................. A61B 5/02
(52) U.S. Cl. ...................... 600/502; 600/500; 600/501
(58) Field of Search ............................... 600/500–503, 600/481, 483, 372, 382, 384

(56) References Cited

U.S. PATENT DOCUMENTS

| | | | | |
|---|---|---|---|---|
| 4,715,384 A | * | 12/1987 | Tabata ......................... 600/519 |
| 5,337,753 A | * | 8/1994 | Lekhtman .................... 600/519 |
| 5,365,934 A | * | 11/1994 | Leon et al. .................. 600/517 |
| 6,115,629 A | * | 9/2000 | Richter ........................ 600/520 |
| 6,165,129 A | * | 12/2000 | Bates .......................... 600/481 |
| 6,506,153 B1 | * | 1/2003 | Littek et al. ................ 600/301 |
| 6,522,255 B1 | * | 2/2003 | Hsieh .......................... 340/657 |

* cited by examiner

Primary Examiner—Max F. Hindenburg
Assistant Examiner—Navin Natnithithadha
(74) Attorney, Agent, or Firm—Birch, Stewart, Kolasch & Birch, LLP

(57) ABSTRACT

The present invention discloses a contact type of pulse measurement device, which comprises a first active sensor electrode and a second active sensor electrode having corresponding opposite polarities with each other; and the two active sensor electrodes respectively connected to the pulse measurement device by conductive wires and the pulse measurement device comprises a negative feedback difference common mode signal and a buffer/balanced circuit for providing a circuit with a self common point electrode potential. Therefore, the first bio-potential signal can be detected by means of the first active sensor electrode and the common point electrode. Similarly, a second bio-potential signal having the same magnitude but a different phase as the first bio-potential signal can be detected by the second active sensor electrode and the common point electrode.

4 Claims, 4 Drawing Sheets

CONTACT TYPE PULSE MEASUREMENT DEVICE

FIELD OF THE INVENTION

The present invention relates to a contact type pulse measurement device, more particularly to a contact type pulse measurement device installed in handheld equipment for measuring the pulse of a user when the user holds such device by a hand.

BACKGROUND OF THE INVENTION

At present, there are two general methods used for measuring the heartbeat rate of exercisers when using sport equipments for the exercise. One method detects the change of blood density in the human skin for the pulse measurement, and the other method detects the potential signal produced by the weak amplitude of vibration of the current, which is the so-called bio-potential signal for the pulse measurement. For the method using the change of blood density in the exerciser's skin for the pulse measurement, a device such as a clamp or a bracelet is generally used to be fixed onto the exerciser's body. However, the device using a clamp or a bracelet is movable and thus the electric wire may be exposed partially. The device will be moved and the electric wire will be shaken or twisted when the exerciser is doing exercises. The displacement of the device and the interference of the conductive wire according to the foregoing phenomenon directly affect the computation for measuring the heartbeat rate with respect to the microprocessor of the system, so that the measured value of the heartbeat rate may be inaccurate and results in a large error. In the meantime, the conductive wire also affects the direction or is in the way of the of the exerciser's movement.

Further, a bio-potential signal is used for the pulse measurement by directly putting an electrode sensor of the fitness equipment in contact with the human body, so that the conductive wire will not vibrate and thus overcoming the shortcoming of causing interferences. Since the current bio-potential signal measuring device (as shown in FIG. 1) requires two electrode sensors, which are a pair of corresponding sets including a first active sensor electrode 10a with a first common point sensor electrode 10b and a second active sensor electrode 10d with a second common point sensor electrode 10c (wherein the foregoing first common point sensor electrode 10b and the second common point sensor electrode 10c are connected together to form the same potential). The two sets of electrode sensors are connected to a pulse measurement device 10 by a conductive wire 101, 102, 103, 104, and the pulse measurement device 10 comprises a bio-potential detector 11 connected to the foregoing two sets of electrode sensors, a bio-signal measurement 12 for receiving the signal transmitted from the bio-potential sensor 11, an analog filter/amplifier 13 for receiving the signal transmitted from the bio-signal measurement 12, and an associative processing unit 14 for receiving the signal processed by the analog filter/amplifier unit 13 for the processing or comparison of related settings, a signal processing unit 15 for processing the signal and displaying a pulse data on a display device 17 and also feeding back the signal to the associative processing unit 14 for the interactive processing. Further, the associative processing unit 14 can be connected to an external input device 16 for entering data or related settings.

Although the foregoing device does not have shaking conductive wires anymore and can overcome the shortcoming of having interferences, each of the two sets of electrode sensors at the gripping positions of the left and right hands should have a first active sensor electrode 10a and a first common point sensor electrode 10b (a second active sensor electrode 10d and a second common point sensor electrode 10c). A user has to hold the first active sensor electrode 10a and the first common point sensor electrode 10b with one hand and the second active sensor electrode 10d and the second common point sensor electrode 10c with the other hand for its use, so that the user's bio-potential is detected by the first active sensor electrode 10a and the first common point sensor electrode 10b (or the second active sensor electrode 10d and the second common point sensor electrode 10c) through the user's hand. However, a hand is holding the first active sensor electrode 10a and the first common point sensor electrode 10b (or the second active sensor electrode 10d and the second common point sensor electrode 10c), and it will reduce the contact area of the electrode sensor and affect the reliability of receiving the signals. Therefore, when a user is doing exercise, the user may have small hands or wants to change gestures or is afraid of not able to grip the first active sensor electrode 10a and the first common point sensor electrode 10b (or the second active electrode sensor 10d and the second common point sensor 10c) at the same time, it will affect the measured value of the pulse.

SUMMARY OF THE INVENTION

The primary objective of the present invention is to provide a solution to overcome the foregoing shortcomings and avoid the existing deficiency by providing a contact type of pulse measurement in accordance with the present invention. The present invention aims at the present shortcoming of the prior-art electrode sensors that requires users to hold a first active sensor electrode and a common point sensor electrode (or a second active sensor electrode and a second common point sensor electrode) to develop a contact pulse measurement device of the present invention that only requires one hand to grip an electrode sensor. As long as the electrode sensor fits the shape of the installed equipment, it will provide a larger contact area for gripping, and users can freely make adjustments to their gestures.

To achieve the foregoing objectives, the contact type pulse measurement device of the present invention is a pulse measurement device installed onto various kinds of handheld equipments, so that users can detect the pulse condition by holding the device which comprises a first active sensor electrode and a second sensor electrode having opposite polarities with each other, and the two active sensor electrodes respectively connected to the pulse measurement device by conductive wires, and the pulse measurement device comprises a bio-potential sensor connected to the foregoing two electrode sensors, a bio-signal measurement for receiving the signal transmitted from the foregoing bio-potential sensor, and the bio-signal measurement is connected to a negative feedback difference common mode signal and a buffer/balance circuit, and the buffer/balance circuit feeds back the signal to the signal measuring device, and the foregoing two sets of units provide a circuit with a common point electrode potential such that the negative feedback difference common mode signal and the buffer/balance circuit provide a circuit with a self common point electrode potential. Therefore, the first bio-potential signal can be detected by means of the first active sensor electrode and the common point electrode. Similarly, a second bio-potential signal having the same magnitude but a different phase as the first bio-potential signal can be detected by the second active sensor electrode and the common point electrode. When the contact type pulse measurement device uses such mechanism to measure biological signals, it only needs to have a sensor at the position of both hands to achieve the function of measuring pulses.

DETAILED DESCRIPTION OF THE PREFERRED EMBODIMENTS

To understand the objective of the invention, its structure, innovative features, and performance, we use a preferred embodiment and the attached drawings for the detailed description of the invention.

Figure 1:
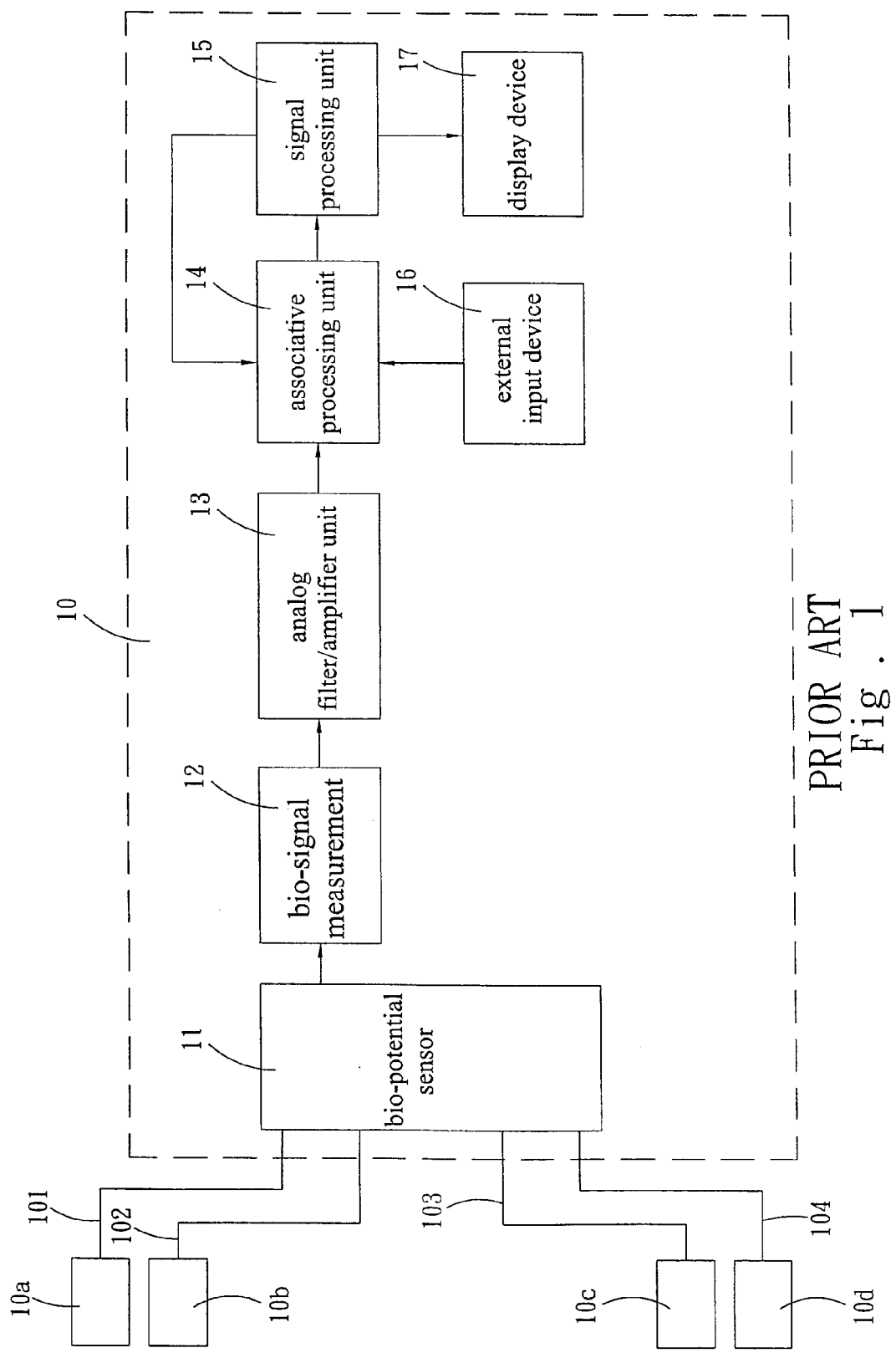
FIG. 1 is a circuit block diagram according to a prior art.
Figure 2:
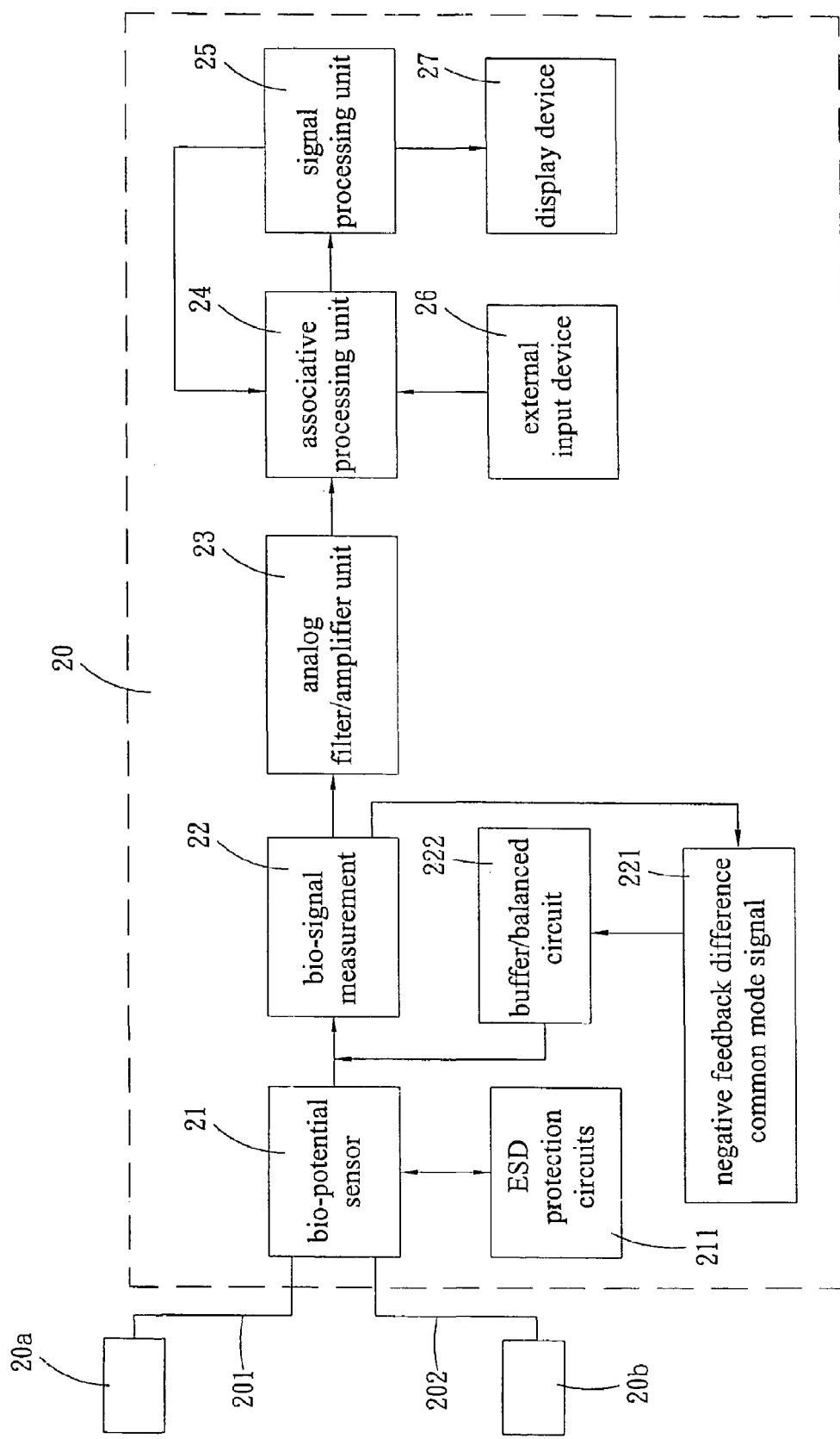
FIG. 2 is a circuit block diagram according to the present invention.

Please refer to FIG. 2 for the circuit block diagram of the present invention. In FIG. 2, a contact type pulse measurement device is a pulse measurement device installed to all kinds of handheld equipments, so that a user can grip the pulse measurement device to measure the pulse condition; wherein the contact pulse measurement device of the invention comprises a first active sensor electrode 20a and a second active sensor electrode 20b having opposite polarities with each other, and the two active sensor electrodes 20a, 20b are connected to a pulse measurement device 20 respectively by conductive wires 201, 202.

Unlike the prior art, the pulse measurement device 20 of the present invention comprises a bio-potential sensor 21 for connecting the foregoing two active sensor electrodes 20a, 20b to detect a bio-potential of human body from user's hands in contact with the first active sensor electrode 20a and the second active sensor electrode 20b; a bio-signal measurement 22 for measuring the signal transmitted from the bio-potential measuring device 21; a negative feedback difference common mode signal 221 and a buffer/balanced circuit 222 being connected to the bio-signal measurement 22 for feeding back a signal to the bio-signal measurement 22 and thus providing a circuit with a self common point electrode potential. The present invention makes use of a negative feedback difference common mode signal 221 and a buffer/balanced circuit 222 to provide a circuit with a self common point electrode potential to cope with the first active sensor electrode 20a and the second active sensor electrode 20b. When the pulse measurement device 20 of the invention measures the biological signal, it only requires one electrode sensor at the contact position of both hands. In the meantime, the bio-potential sensor 21 is connected to a ESD (Electro-Static Discharges) protection circuits 211 for protecting the pulse measurement device 20 from being damaged by the surge of external voltage.

Further, an analog filter/amplifier unit 23 for receiving signals transmitted from the foregoing bio-signal measurement 22 is used to filter and amplify the signal amplitude of within the electro-cardio frequency of the measured signal and facilitate the application later.

An associative processing unit 24 receives the signal filtered and amplified by the foregoing analog filter/amplifier unit 23 to the process or compare parameter settings. A signal processing unit 25 will display a processed signal (such as a heart rate count or a comparison of standard heart rate value) on a display device 27 and shows the user's heart rate data or related information. In the meantime, the signal processing unit 25 also feeds the signal parameter back to the foregoing associative processing unit 24 for the setup of the system parameters. Further, an associative processing unit 24 is connected to an input device 26, so that users can enter external data or related parameter settings to the associative processing unit 24.

Further, a display device 27 can be detached from the pulse measurement device 20 and integrated with a screen display of the system in which the pulse measurement device 20 is installed.

The pulse measurement device 20 of the present invention mainly uses a negative feedback difference common mode signal 221 and a buffer/balanced circuit 222 to provide a circuit with a self common point electrode potential. Therefore, the user's bio-potential signals can be detected by the first active sensor electrode 20a and the common point electrode. In the meantime, another bio-potential signal having the same magnitude but different phases will be detected by the second active sensor electrode 20b and the common electrode. When such mechanism of the contact type pulse measurement device 20 is used to measure biological signals, it only requires one electrode sensor at the contact positions of both hands to achieve the function of measuring pulses.

Figure 3:
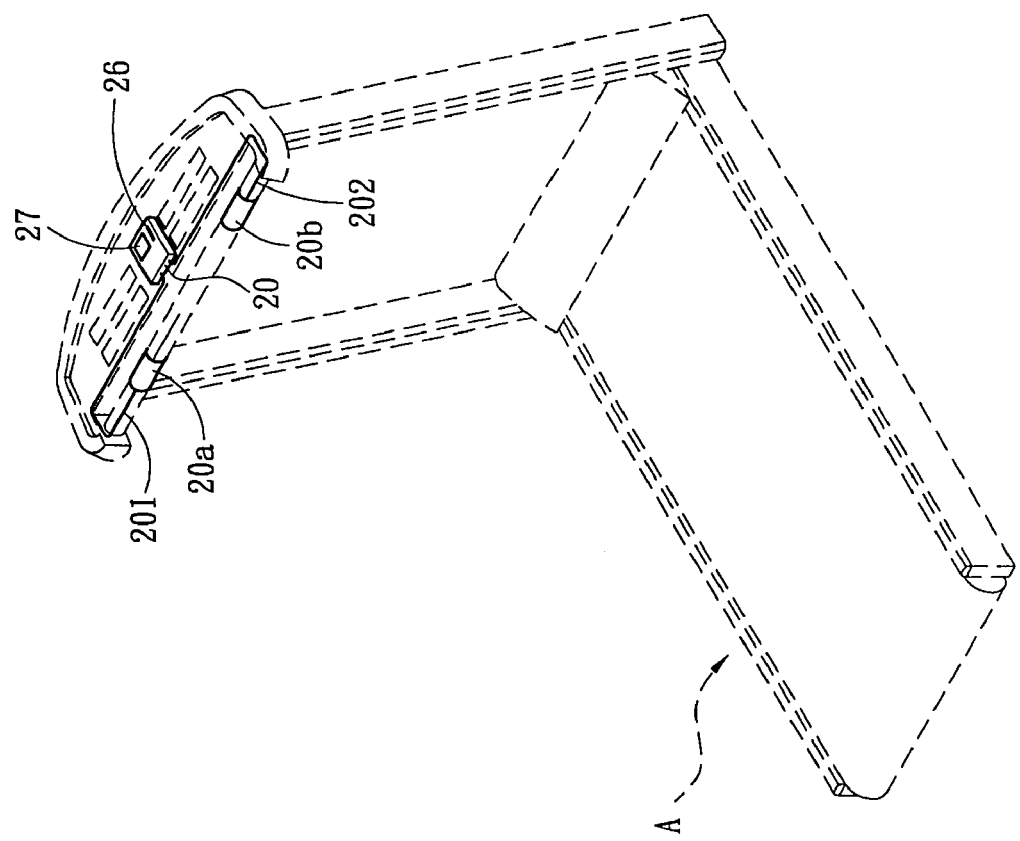
FIG. 3 is a view of the treadmill according to the present invention when it is in use.

Please refer to FIG. 3 for an illustrative view of the treadmill according to the present invention when it is in use. In the figure, a first active sensor electrode 20a and a second active sensor electrode 20b are disposed at the user's handrail of a treadmill A. The pulse measurement device 20 is installed at an obvious and convenient location for the user to read the heart rate data or related information easily through a display device 27, and the pulse measurement device 20 has an input device 26 on one side, so that a user can enter external data or related settings to the internal components of the pulse measurement device 20.

Figure 4:
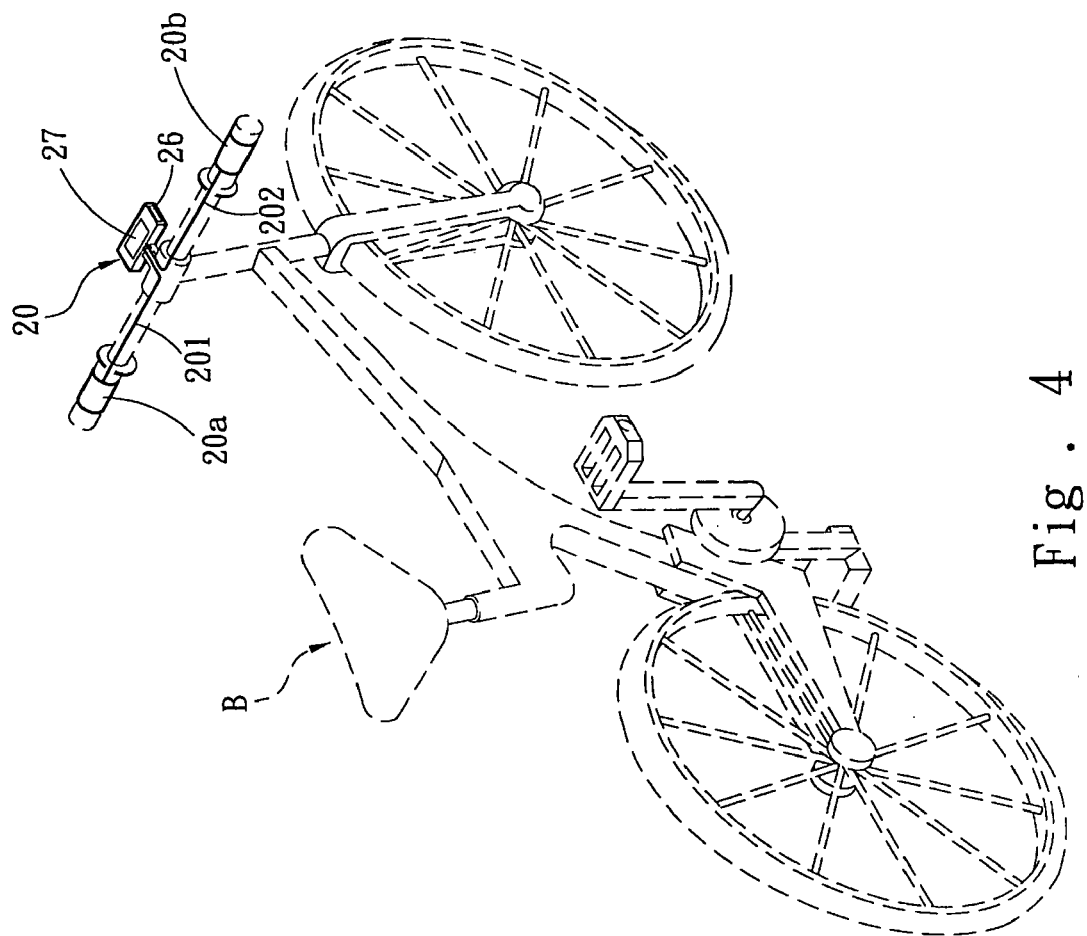
FIG. 4 is a view of the fitness bicycle according to the present invention.

Please refer to FIG. 4 for the illustrative view of a fitness bicycle according to the present invention when it is in use. In the figure, the first active sensor electrode 20a and the second active sensor electrode 20b of the present invention are disposed at the handle of the fitness bicycle B, and the pulse measurement device 20 is installed at the middle of the handlebar of the fitness bicycle B so that the user can read the heart rate data or related information easily from the display device 27. Further, an input device 26 is disposed on one side of the pulse measurement device 20 so that the user can enter external data or related settings to the internal components of the pulse measurement device 20.

What is claimed is:

1. A contact type pulse measurement device, installed to a handheld equipment for measuring a pulse condition of a user holding said device by a hand, wherein said contact type pulse measurement device comprising:

a first active sensor electrode and a second active sensor electrode having corresponding opposite polarities with each other, and said two active sensor electrodes respectively coupled with said pulse measurement device by a conductive wire;

a bio-potential sensor, coupled to said two active sensor electrodes;

a bio-signal measurement unit for receiving a signal transmitted from said bio-potential sensor and coupling to a negative feedback difference common mode signal unit and a buffer/balanced circuit, wherein said buffer/balance circuit feeds back a signal from said negative feedback difference common mode signal unit to said bio-signal measurement unit, and wherein said both negative feedback difference common mode signal unit and buffer/balanced circuit providing a circuit with a self common point electrode potential;

an analog filter/amplifier for receiving a signal transmitted from said bio-signal measurement;

an associative processing unit, to receiving a signal processed by said analog filter/amplifier for selectively process and compare a parameter setting; and a signal processing unit for displaying a pulse data on a display device after said signal is processed and feeding said signal back to said associative processing unit to set a system parameter.

2. The contact type pulse measurement device of claim 1, wherein said bio-potential sensor is coupled to a Electro-Static Discharge protection circuits to protect said contact type pulse measurement device from being damaged by a surge voltage.

3. The contact type pulse measurement device of claim 1, wherein said associative processing unit is externally connected to an input device to selectively enter data and a related setting.

4. The contact type pulse measurement device of claim 1, wherein said display device is detached from said pulse measurement device and integrated with a screen display of a system in which said pulse measurement device is installed.

* * * * *